United States Patent
Matsuoka

(10) Patent No.: US 10,067,047 B2
(45) Date of Patent: Sep. 4, 2018

(54) PARTICLE DETECTION SYSTEM

(71) Applicant: NGK SPARK PLUG CO., LTD., Nagoya-shi, Aichi (JP)

(72) Inventor: Toshiya Matsuoka, Kaizu (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 368 days.

(21) Appl. No.: 14/794,245

(22) Filed: Jul. 8, 2015

(65) Prior Publication Data

US 2016/0011093 A1    Jan. 14, 2016

(30) Foreign Application Priority Data

Jul. 8, 2014   (JP) ................................. 2014-140935
Jun. 3, 2015   (JP) ................................. 2015-113467

(51) Int. Cl.
*G01N 15/06* (2006.01)
*G01M 15/10* (2006.01)
*G01N 15/00* (2006.01)

(52) U.S. Cl.
CPC ...... *G01N 15/0656* (2013.01); *G01M 15/102* (2013.01); *G01N 2015/0046* (2013.01)

(58) Field of Classification Search
CPC ............ G01M 15/102; G01N 15/0656; G01N 2015/0046
See application file for complete search history.

(56) References Cited

U.S. PATENT DOCUMENTS

2012/0247181 A1* 10/2012 Nishijima .......... G01N 15/0656
                                                      73/23.33
2012/0291632 A1* 11/2012 Nishijima ............... F01N 11/00
                                                      96/421
2012/0312074 A1   12/2012 Allmendinger et al.
2013/0219990 A1    8/2013 Allmendinger et al.
2014/0352405 A1* 12/2014 Motomura ......... G01N 15/0656
                                                      73/23.31

FOREIGN PATENT DOCUMENTS

JP    2012-219673 A     11/2012
JP    2013-170914 A      9/2013
WO   WO 2013/136745  *   9/2013  .............. F01N 11/00

OTHER PUBLICATIONS

Japan Patent Office, Office Action (Notification of Reasons for Refusal) entered in corresponding Application No. JP2015-113467, dated May 23, 2018.

* cited by examiner

*Primary Examiner* — Daniel S Larkin
(74) *Attorney, Agent, or Firm* — Stites & Harbison, PLLC; Jeffrey A. Haeberlin; James R. Hayne

(57) ABSTRACT

A particle detection system includes a sensor main body having an electrification section for electrifying particles contained in a gas under measurement so as to produce electrified particles, and detects the particles contained in the gas under measurement by using the electrified particles. The sensor main body has a heater portion which generates heat upon energization so as to heat at least a portion of the electrification section. The particle detection system detects a burnable period (for example, fuel cut period) during which the gas under measurement contains oxygen for burning particles adhering to the electrification section, and energizes the heater portion during the burnable period so as to heat at least a portion of the electrification section to a temperature at which the adhering particles burn.

5 Claims, 11 Drawing Sheets

PARTICLE DETECTION SYSTEM

BACKGROUND OF THE INVENTION

Technical Field

The present invention relates to a particle detection system for detecting particles contained in a gas under measurement.

Description of the Related Art

Conventionally, there has been known a particle detection system which includes a sensor main body having an electrification section for electrifying particles such as soot contained in a gas under measurement to thereby produce electrified particles and which detects the particles contained in the gas under measurement through use of the electrified particles. A specific example of such a particle detection system is a particle detection system whose electrification section includes an ion source for producing ions through corona discharge and which electrifies particles (soot or the like) contained in exhaust gas using the produced ions, to thereby detect the amount of particles contained in the exhaust gas. Patent Document 1 discloses a particle detection system which is mounted on a vehicle including a diesel engine and in which a particle sensor 100 serving as a sensor main body and a sensor drive section 110 for controlling the particle sensor 100 are connected through a cable 120. Also, Patent Documents 2 and 3 disclose a particle detection system whose electrification section includes a pair of electrodes overlapping each other to form the shape of a double-wall tube and in which, after PM agglomerates (PM structures (particulate matter structures)); i.e., particles adhering to the surfaces of the electrodes, are previously formed through use of particles contained in a gas under measurement flowing through the space between the electrodes, the gas under measurement is caused to flow, a high voltage is applied between the electrodes to produce electrified PM agglomerates which move between the electrodes, and the particles are detected through use of the electrified PM agglomerates.

Meanwhile, such a particle detection system may lower in particle detection performance or may become unable to detect particles as a result of accumulation of particles on the electrification section. Therefore, some particle detection systems have a heater which burns and removes particles adhering to the electrification section of the sensor main body. For example, in the particle detection system of Patent Document 1, a heater pattern 380 is provided in a sensor unit 300 which is formed of an insulating ceramic and is provided in the particle sensor 100 (the sensor main body). This heater pattern 380 heats the entirety of the sensor unit 300 to 550 to 600° C. to thereby burn soot adhering to a first electrode 322 of a discharge pattern 320, etc.

PRIOR ART DOCUMENTS

Patent Document 1 is Japanese Patent Application Laid-Open (kokai) No. 2013-170914.

Patent Document 2 is United State Patent Application Laid-Open (kokai) No. US2012/0312074A1.

Patent Document 3 is United State Patent Application Laid-Open (kokai) No. US2013/0219990A1.

BRIEF SUMMARY OF THE INVENTION

As disclosed in Patent Document 1 as well, these particle detection systems have conventionally been intended for use with diesel engines, which produce a large amount of soot. However, in recent years, since direct-injection-type gasoline engines have spread and emission control has become stricter, such a particle detection system is used for some gasoline engines.

In the case where a particle detection system is used for a diesel engine, since some amount of oxygen gas is contained (remains) in exhaust gas, no special restriction is imposed on the timing of burning and removing adhering particles such as soot by heating them by a heater.

However, in the case of a gasoline engine, combustion is basically performed at the stoichiometric air-fuel ratio. Therefore, in the case where the air-fuel ratio is on the rich side of the stoichiometric air-fuel ratio, oxygen is hardly present in exhaust gas. In such exhaust gas, even when the heater is energized to generate heat, adhering particles (soot, etc.) cannot be burnt.

In addition, in the case where electricity is always supplied to the heater so as to allow the heater to burn adhering particles at any time, useless energy consumption (power consumption) occurs at the heater.

The present invention has been accomplished in view of such a problem, and its object is to provide a particle detection system which can properly burn and remove particles adhering to an electrification section.

One mode of the present invention is a particle detection system which includes a sensor main body having an electrification section for electrifying particles contained in a gas under measurement so as to produce electrified particles and which detects the particles contained in the gas under measurement by using the electrified particles, wherein the sensor main body has a heater portion for heating at least a portion of the electrification section; and the particle detection system comprises period detection means for detecting a burnable period during which the gas under measurement contains oxygen for burning particles adhering to the electrification section, and heater energization control means for energizing the heater portion during the burnable period so as to heat at least a portion of the electrification section to a temperature at which the particles adhering to the electrification section burn.

In this particle detection system, the burnable period during which oxygen gas necessary for burning particles adhering to the electrification section is present in the gas under measurement is detected, and energization of the heater portion is performed during this burnable period. As a result, the particles adhering to the electrification section can be removed properly, whereby the detection performance of the sensor main body can be maintained. Meanwhile, since the heater portion is not energized at all times, unnecessary energy consumption (power consumption) at the heater portion can be suppressed.

Notably, the electrification section may be a section which includes an ion source for generating ions by means of gaseous discharge and which causes the generated ions to adhere to particles floating within the gas under measurement so as to electrify the particles to thereby produce electrified particles. Alternatively, the electrification section may be a section in which, after particles contained in a gas under measurement are previously caused to adhere to the surfaces of a pair of electrodes to thereby form PM agglomerates, the gas under measurement is caused to flow, and a high voltage is applied between the electrodes to thereby produce charged particles (electrified PM agglomerates) which move between the surfaces of the electrodes.

Also, in the case where the gas under measurement is exhaust gas discharged from an internal combustion engine of an automobile, an example of the burnable period is a fuel cut period during which the supply of fuel to the internal combustion engine is stopped at the time of deceleration or the like. During such a fuel cut period, since the supply of fuel to the internal combustion engine is stopped, instead of combustion gas, air (outside air) flows through the exhaust pipe. Accordingly, during the fuel cut period, oxygen gas necessary for burning adhering particles is sufficiently present in the gas under measurement. Other examples of the burnable period include an idling stop period during which the internal combustion engine is automatically stopped when the vehicle temporarily stops, for example, until a traffic light changes, and a lean burn operation period during which the internal combustion engine is operated by lean burn at an air-fuel ratio on the lean side with respect to the stoichiometric air-fuel ratio. In the case of a hybrid vehicle, a period during which the internal combustion engine stops and the vehicle is traveling by a motor may be contained in the burnable period.

Examples of a method of detecting the burnable period include a method of detecting a signal output from an external engine control unit (ECU) and representing the burnable period such as a fuel cut period, and a method of utilizing the output of an oxygen sensor for measuring the oxygen concentration of the gas under measurement so as to detect a burnable period during which the oxygen concentration is equal to or higher than a predetermined level. Namely, the period detection means is preferably configured to detect a burnable period during which the gas under measurement contains oxygen gas at a concentration at which the particles adhering to the electrification section burn.

Further, the above-described particle detection system is preferably configured in such a manner that the electrification section includes an ion source for producing ions through gaseous discharge and causes the produced ions to adhere to the particles floating in the gas under measurement to thereby electrify the particles and produce the electrified particles; and the heater portion heats at least a portion of the ion source of the electrification section.

In this particle detection system, the electrification section includes an ion source for producing ions through gaseous discharge and causes the produced ions to adhere to the particles floating in the gas under measurement to thereby electrify the particles and produce the electrified particles. The heater portion heats at least a portion of the ion source. By virtue of this configuration, it is possible to heat the ion source during the burnable period to thereby properly remove the particles adhering to the ion source. As a result, it is possible to suppress a drop in detection performance which is caused by a failure to generate ions properly.

Further, the above-described particle detection system is preferably configured in such a manner that the period detection means is signal detection means for detecting input of a burnable signal externally supplied and indicating the burnable period; and the heater energization control means includes energization switching means for switching the state of supply of electricity to the heater portion in accordance with the detected burnable signal.

The period detection means of this particle detection system is signal detection means, and the heater energization control means includes energization switching means.

In this system, since the supply of electricity to the heater portion is switched in accordance with the burnable signal from the outside, it is possible to energize the heater portion at a proper timing to thereby reliably burn and remove the particles adhering to the electrification section.

Notably, an example of such a burnable signal is a signal output from the ECU and representing the above-described burnable period such as the fuel cut period, idling stop period, or lean burn operation period of the internal combustion engine.

Also, examples of a method of switching the electricity supplied to the heater portion include a method of starting and stopping the supply of electricity to the heater portion in accordance with the burnable signal, and a method of switching the magnitude of the electric power supplied to the heater portion (the magnitude of the effective voltage; the magnitude of the duty ratio) in accordance with the burnable signal in such a manner that the electric power increases during the burnable period and decreases during periods other than the burnable period.

Further, the above-described particle detection system is preferably configured in such a manner that the gas under measurement is exhaust gas discharged from an internal combustion engine; and the burnable signal is a signal indicating that the internal combustion engine is in a fuel cut period, an idling stop period, or a lean burn operation period.

In this particle detection system, since the burnable period such as fuel cut period can be known from the burnable signal, it is possible to properly burn and remove the particles adhering to the electrification section.

Further, the above-described particle detection system is preferably configured in such a manner that the heater energization control means includes energization stoppage means for stopping the energization when a duration time of the energization of the heater portion having started in the burnable period exceeds a predetermined time.

Even after the supply of electricity to the heater portion is started during the burnable period and the particles adhering to the electrification section are removed by heating by the heater section, the energization of the heater portion may be continued. However, this may result in consumption of energy (power) by the heater portion. In order to overcome such a drawback, in this particle detection system, when the duration time of the energization of the heater portion having started in the burnable period exceeds the predetermined time, the energization of the heater portion is stopped even if it is in the middle of the burnable period. As a result, the useless energy consumption (power consumption) at the heater portion can be further suppressed.

DETAILED DESCRIPTION OF EXEMPLARY EMBODIMENTS OF THE INVENTION

Figure 1:
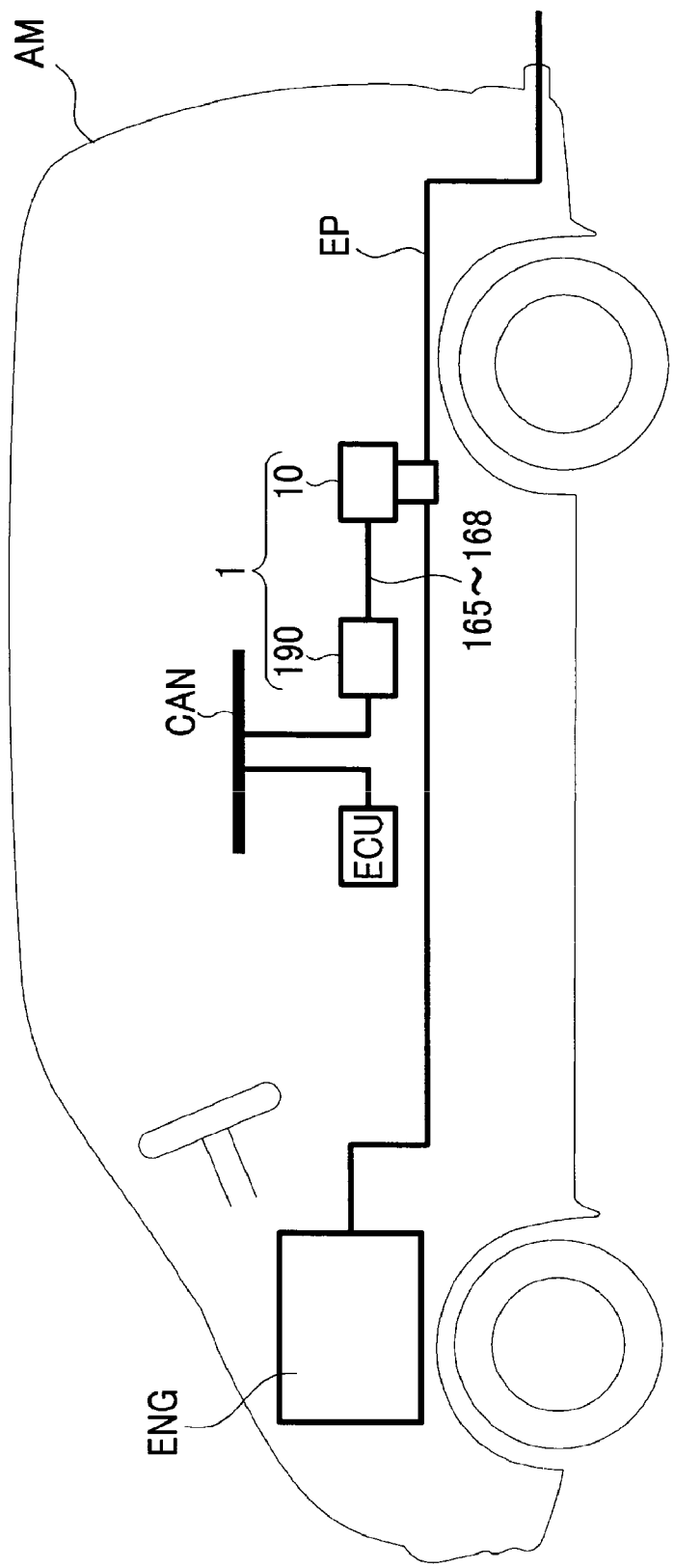
FIG. 1 is an explanatory view relating to an embodiment and describing a state in which a particle detection system is applied to an exhaust pipe of an engine mounted on a vehicle.

An embodiment of the present invention will be described with reference to the drawings. As shown in FIG. 1, a particle detection system 1 (hereinafter simply referred to as the system 1) of the present embodiment is attached to an exhaust pipe EP of an engine ENG (internal combustion engine) mounted on a vehicle AM, and detects particles S (soot, etc. shown, for example, in FIG. 7) contained in exhaust gas EG (gas under measurement shown, for example, in FIGS. 3 and 7) flowing through the exhaust pipe EP. Notably, in the present embodiment, the engine ENG of the vehicle AM is a direct-injection-type gasoline engine.

Also, this system 1 is composed of a sensor main body 10, a circuit section 190, and cables 165 to 168 connecting them.

Figure 3:
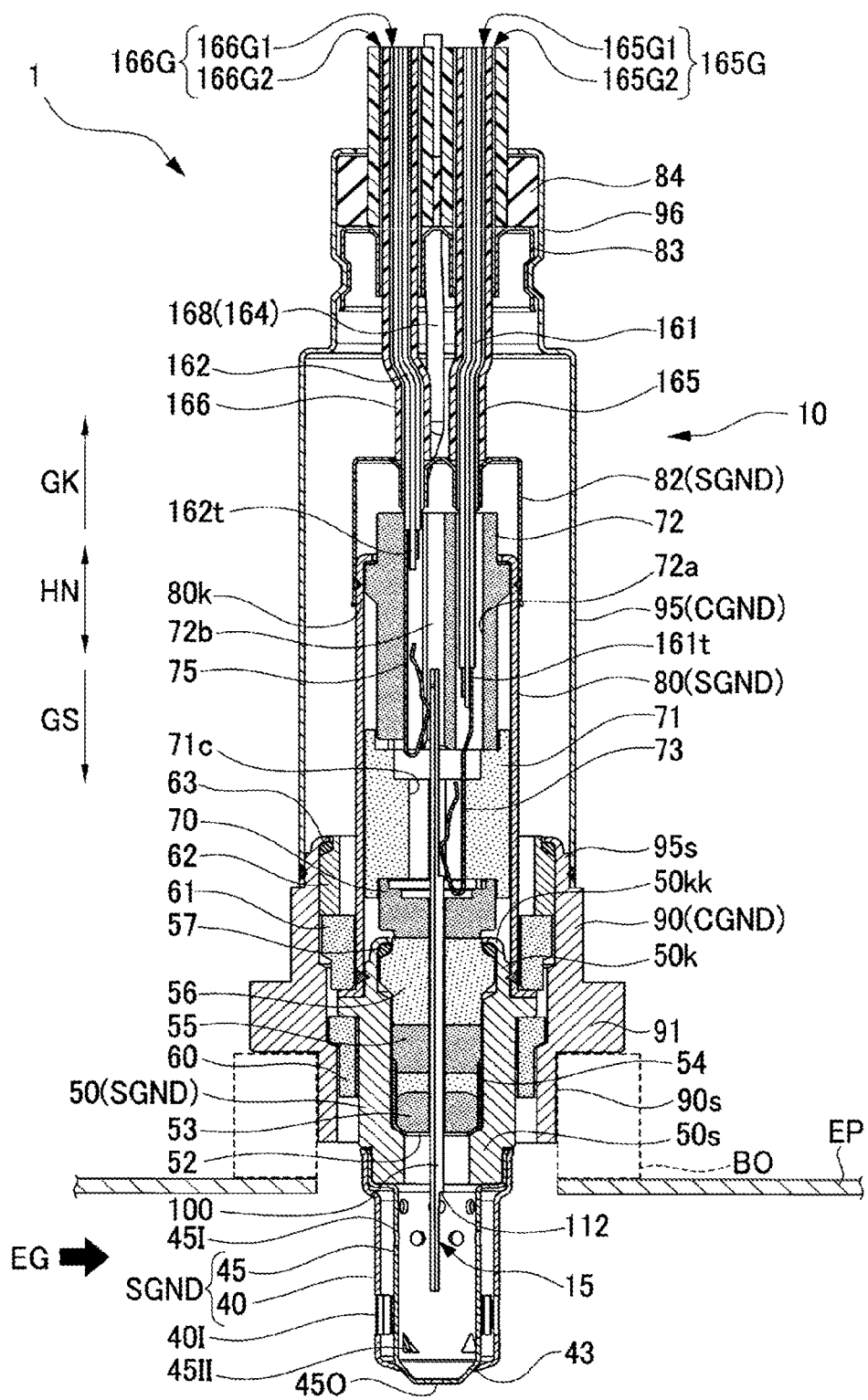
FIG. 3 is a longitudinal sectional view of a sensor main body of the particle detection system according to the embodiment.

The sensor main body 10 is fixed to the exhaust pipe EP, and its portion on the forward end side is disposed within the exhaust pipe EP and is in contact with the exhaust gas EG (see FIG. 3).

The circuit section 190 is connected to the sensor main body 10 through the cables 165 to 168 and includes a circuit which drives the sensor main body 10 and detects a signal current Is to be described later.

Of the cables 165 to 168, each of the cables 165 and 166 is a triple coaxial cable (triaxial cable), and each of the cables 167 and 168 is a single-conductor insulating cable having a small diameter. The cable 165 includes a discharge potential lead wire 161 as a core wire (center conductor), and the cable 166 includes an auxiliary potential lead wire 162 as a core wire (center conductor). Also, the cable 167 includes a first heater lead wire 163 as a core wire, and the cable 168 includes a second heater lead wire 164 as a core wire (see FIGS. 2 and 3).

First, the schematic configuration of the circuit section 190 of the present system 1 will be described with reference to FIG. 2. The circuit section 190 has a measurement control circuit 220 which includes a signal current detection circuit 230 and a heater energization circuit 226; an ion source power supply circuit 210; and an auxiliary electrode power supply circuit 240.

The ion source power supply circuit 210 has a first output terminal 211 maintained at a sensor GND potential SGND and a second output terminal 212 maintained at a discharge potential PV2. The second output terminal 212 is connected to the discharge potential lead wire 161. The discharge potential PV2 is set to a positive high potential, specifically, with respect to the sensor GND potential SGND (reference). Notably, the ion source power supply circuit 210 constitutes a constant-current power supply whose output current is feedback-controlled such that the output current (effective value) is autonomously maintained at a predetermined current value (for example, 5 μA).

Meanwhile, the auxiliary electrode power supply circuit 240 has an auxiliary first output terminal 241 maintained at the sensor GND potential SGND, and an auxiliary second output terminal 242 maintained at an auxiliary potential PV3. The auxiliary second output terminal 242 is connected to the auxiliary potential lead wire 162. The auxiliary potential PV3 is set to a potential of, for example, DC 100 to 200 V which is a positive high DC potential, specifically, with respect to the sensor GND potential SGND (reference) but is lower than the peak potential of the discharge potential PV2.

Moreover, the signal current detection circuit 230, which partially constitutes the measurement control circuit 220, has a signal input terminal 231 connected to the first output terminal 211 of the ion source power supply circuit 210, which is maintained at the sensor GND potential SGND, and a ground input terminal 232 connected to a chassis GND potential CGND. Notably, the chassis GND potential CGND and the sensor GND potential SGND are insulated from each other, and the signal current detection circuit 230 detects the signal current Is flowing between the signal input terminal 231 (the sensor GND potential SGND) and the ground input terminal 232 (the chassis GND potential CGND).

Also, the heater energization circuit 226 is a circuit for supplying electricity to a heater portion 130 of a ceramic element 100, which will be described later, through PWM control. The heater energization circuit 226 has a first heater energization terminal 226a connected to the first heater lead wire 163 and a second heater energization terminal 226b connected to the second heater lead wire 164. Notably, the second heater energization terminal 226b and the second heater lead wire 164 communicate with the chassis GND potential CGND and are maintained at the chassis GND potential CGND. Also, the first heater energization terminal 226a and the first heater lead wire 163 have a potential with respect to the chassis GND potential CGND (reference).

In addition, in this circuit section 190, the ion source power supply circuit 210 and the auxiliary electrode power supply circuit 240 are surrounded by an inner circuit case 250 maintained at the sensor GND potential SGND. The first output terminal 211 of the ion source power supply circuit 210, the auxiliary first output terminal 241 of the auxiliary electrode power supply circuit 240, and the signal input terminal 231 of the signal current detection circuit 230 are connected to this inner circuit case 250.

Notably, in the present embodiment, this inner circuit case 250 accommodates and surrounds the ion source power supply circuit 210, the auxiliary electrode power supply circuit 240, and a secondary-side core 271B of an isolation transformer 270, and communicates with the first output terminal 211 of the ion source power supply circuit 210 and the auxiliary first output terminal 241 of the auxiliary electrode power supply circuit 240, whereby the inner circuit case 250 is maintained at the sensor GND potential SGND. Also, the first output terminal 211 of the ion source power supply circuit 210 and the auxiliary first output terminal 241 of the auxiliary electrode power supply circuit 240 respectively communicate with inner external conductors 165G1 and 166G1 of coaxial double external conductors 165G and 166G of the cables 165 and 166, the inner external conductors 165G1 and 166G1 being maintained at the sensor GND potential SGND.

Meanwhile, the core 271 of the isolation transformer 270 is divided into a primary-side core 271A around which a primary-side coil 272 is wound and a secondary-side core 271B around which a power-supply-circuit-side coil 273 and an auxiliary-electrode-power-supply-side coil 274 are wound. The primary-side core 271A communicates with the chassis GND potential CGND, and the secondary-side core 271B communicates with the sensor GND potential SGND (the first output terminal 211 of the ion source power supply circuit 210).

Further, the ion source power supply circuit 210, the auxiliary electrode power supply circuit 240, the inner circuit case 250, and the measurement control circuit 220 including the signal current detection circuit 230 and the heater energization circuit 226 are surrounded by an outer circuit case 260 maintained at the chassis GND potential CGND. Further, the ground input terminal 232 of the signal current detection circuit 230, the second heater energization terminal 226b of the heater energization circuit 226, and the primary-side core 271A of the isolation transformer 270 are connected to the outer circuit case 260 and are maintained at the chassis GND potential CGND.

Notably, in the present embodiment, this outer circuit case 260 accommodates and surrounds the ion source power supply circuit 210, the auxiliary electrode power supply circuit 240, the inner circuit case 250, the measurement control circuit 220 including the signal current detection circuit 230 and the heater energization circuit 226, and the primary-side core 271A of the isolation transformer 270. Further, this outer circuit case 260 communicates with outer external conductors 165G2 and 166G2 of the coaxial double external conductors 165G and 166G of the cables 165 and 166, the outer external conductors 165G2 and 166G2 being maintained at the chassis GND potential CGND.

The measurement control circuit 220 includes a regulator power supply PS. This regulator power supply PS is connected, through a power supply cable BC, to an external battery BT mounted on the vehicle AM, and is driven by the battery BT. Also, the GND potential of the battery BT is made common with the chassis GND potential CGND.

Also, the measurement control circuit 220 includes a microprocessor 202, and can communicate, through a communication line CC (specifically, through a CAN bus as shown in FIG. 1), with a control unit ECU which controls the engine ENG. Thus, the measurement control circuit 220 can transmit to the control unit ECU, for example, the measurement result (the magnitude of the signal current Is) of the above-described signal current detection circuit 230 or a value obtaining by converting it to the amount of particles. Further, a particle detection start instruction signal ST and a fuel cut signal FC (which will be described later) output from the ECU are input to the measurement control circuit 220 through the communication line CC (CAN bus). The microprocessor 202 can detect these signals.

A portion of the electric power externally supplied to the measurement control circuit 220 through the regulator power supply PS is distributed to the ion source power supply circuit 210 and the auxiliary electrode power supply circuit 240 through the isolation transformer 270. Notably, in the isolation transformer 270, the primary-side coil 272, which partially constitutes the measurement control circuit 220, the power-supply-circuit-side coil 273, which partially constitutes the ion source power supply circuit 210, the auxiliary-electrode-power-supply-side coil 274, which partially constitutes the auxiliary electrode power supply circuit 240, and the core 271 (the primary-side core 271A and the secondary-side core 271B) are insulated from one another. Therefore, it is possible to distribute electric power from the measurement control circuit 220 to the ion source power supply circuit 210 and the auxiliary electrode power supply circuit 240, while maintaining the insulation among them.

Next, the mechanical structure of the sensor main body 10 of the present system 1 will be described with reference to a longitudinal sectional view of FIG. 3 and an exploded perspective view of FIG. 4. Notably, in FIG. 3, the lower side corresponds to the forward end side GS of the sensor main body 10 in the longitudinal direction HN, and the upper side corresponds to the rear end side GK of the sensor main body 10. Also, in FIG. 4, the greater the degree of closeness to the lower side and the right side, the greater the degree of closeness to the forward end side GS of the sensor main body 10.

The sensor main body 10 includes a plate-shaped ceramic element 100 which extends in the longitudinal direction HN and generates ions by means of gaseous discharge. In addition to that, the sensor main body 10 includes a metallic shell 50 which holds the ceramic element 100 in an insulated state and which is maintained at the sensor GND potential SGND; members joined to the metallic shell 50; a mounting metallic member 90 which is insulated from the metallic shell 50, etc., which surrounds and holds these members, and which is attached to the exhaust pipe EP to thereby be maintained at the chassis GND potential CGND; members joined to the mounting metallic member 90; etc.

Specifically, the sensor main body 10 has the tubular mounting metallic member 90 provided on the forward end side GS thereof. The mounting metallic member 90 has a flange portion 91 which projects radially outward so as to form a hexagonal outer shape. A male screw used for attachment to the exhaust pipe EP is formed on the outer circumference of a forward end portion 90s of the mounting metallic member 90 which is located on the forward end side GS in relation to the flange portion 91. By means of the male screw of the forward end portion 90s of the mounting metallic member 90, the sensor main body 10 is attached to an attachment boss BO which is formed of metal and is separately fixed to the exhaust pipe EP, whereby the sensor main body 10 is fixed to the exhaust pipe EP via the attachment boss BO. Therefore, the mounting metallic member 90 is maintained at the chassis GND potential CGND, which is the same as the potential of the exhaust pipe EP.

An outer tube 95 formed of metal is laser-welded to an end of the mounting metallic member 90 on the rear end side GK.

The tubular metallic shell 50 and an inner tube 80 integrated therewith are disposed on the radially inner side of the mounting metallic member 90 with first and second insulating spacers 60 and 61 (formed of an insulating material) interposed therebetween. Also, together with these members, a tubular sleeve 62 and an annular line packing 63 are disposed within the mounting metallic member 90.

Also, a metal cup 52 is disposed within the metallic shell 50, and the plate-shaped ceramic element 100 is inserted into a hole formed in a bottom portion of the metal cup 52. Notably, a portion of the ceramic element 100 projecting from the metal cup 52 toward the forward end side GS forms an ion source 15 which has a needle-shaped electrode portion 112 of a discharge electrode member 110 (which will be described later) at which corona discharge occurs (see FIG. 5). Also, around the ceramic element 100, a tubular ceramic holder 53 formed of alumina, a first powder charged layer 54 formed by compressing powder of talc and holding the ceramic element 100 to the metal cup 52, a second powder charged layer 55 formed by compressing powder of talc and securing gas tightness between the metallic shell 50 and the ceramic element 100, and a tubular ceramic sleeve 56 formed of alumina are disposed in this order from the forward end side GS toward the rear end side GK. Further, a crimp ring 57 is disposed between a rearmost end portion 50kk of the metallic shell 50 and the ceramic sleeve 56, and the rearmost end portion 50kk of the metallic shell 50 is bent radially inward by means of crimping, to thereby press the ceramic sleeve 56 through the crimp ring 57.

Also, protectors, specifically, an inner protector 45 and an outer protector 40 which are formed of stainless steel and form the shape of a double-wall tube, are fixedly provided at a forward end portion 50s of the metallic shell 50, and surrounds a forward end portion of the ceramic element 100 from the radially outer side. The protectors protect the ceramic element 100 from water droplets and foreign substances, and introduce the exhaust gas EG into a space around the ceramic element 100.

A plurality of rectangular outer introduction holes 40I for introducing the exhaust gas EG are formed in the outer protector 40 to be located in a circumferential region on the forward end side GS. Also, a plurality of triangular inner introduction holes 45I and a plurality of circular inner introduction holes d 45II are formed in the inner protector 45 in such a manner that the triangular inner introduction holes 45I are located in a circumferential region on the forward end side GS and the circular inner introduction holes 45II are located in a circumferential region on the rear end side GK.

Further, a circular discharge opening 45O for discharging the introduced exhaust gas EG (gas under measurement) is formed in a forward end portion of the inner protector 45. The forward end portion of the inner protector 45, including the discharge opening 45O, projects outward from an opening 43 of a forward end portion of the outer protector 40.

Here, the inner protector 45 and the outer protector 40 will be described with reference to FIG. 7. Specifically, there will be described the introduction and discharge of the exhaust gas EG into and from the interiors of the inner protector 45 and the outer protector 40 at the time when the sensor main body 10 is used.

Figure 7:
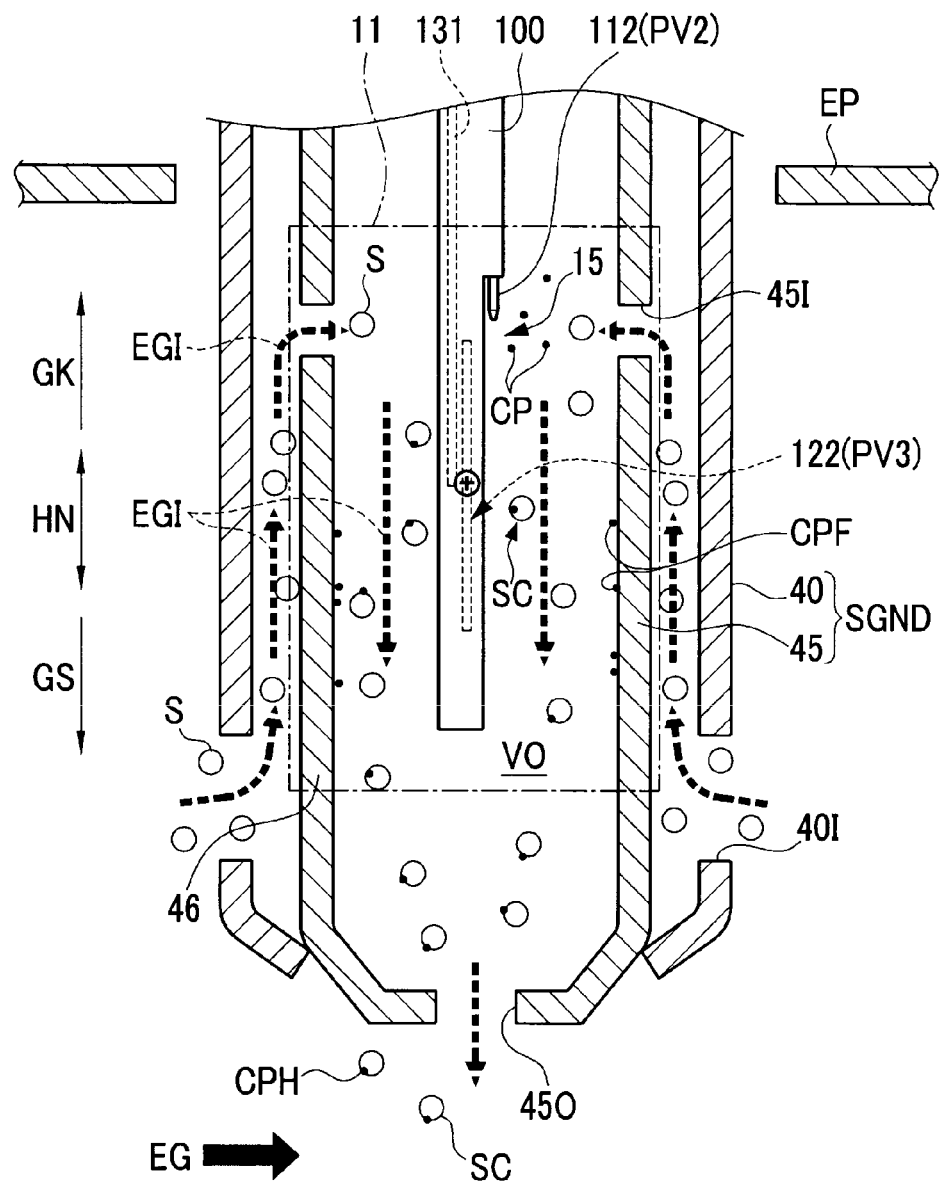
FIG. 7 is an explanatory view schematically showing the electrical function and operation of the particle detection system according to the embodiment, as well as introduction and discharge of exhaust gas.

In FIG. 7, the exhaust gas EG flows within the exhaust pipe EP from the left-hand side toward the right-hand side. When the exhaust gas EG passes through a region around the outer protector 40 and the inner protector 45 of the sensor main body 10, a negative pressure is produced near the discharge opening 45O due to the so-called Venturi effect. By this negative pressure, the exhaust gas EGI introduced into the inner protector 45 is discharged through the discharge opening 45O. Simultaneously, the exhaust gas EG around the outer introduction holes 40I of the outer protector 40 is introduced into the interior of the inner protector 45 through the outer introduction holes 40I of the outer protector 40 and the inner introduction holes 45I of the inner protector 45.

Figure 4:
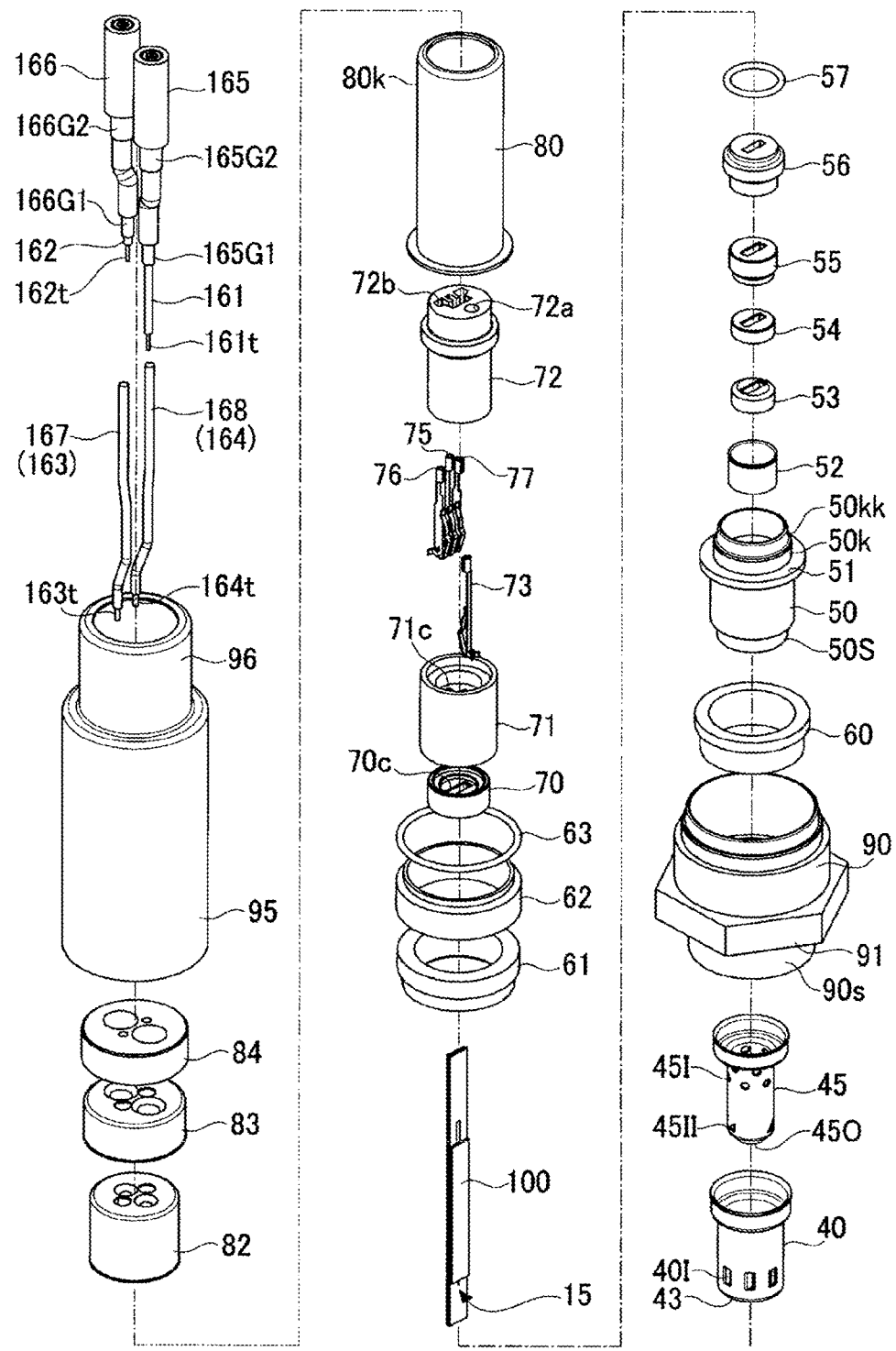
FIG. 4 is an exploded perspective view showing the structure of the sensor main body of the particle detection system according to the embodiment.

Next, resuming the description of the mechanical structure of the sensor main body 10 made with reference to FIGS. 3 and 4, an insulating holder 70 formed of an insulating material is disposed to be located on the outer side (on the rear end side GK) of the metallic shell 50 (i.e., on the rear end side GK of the ceramic sleeve 56) and to be located within the inner tube 80. The ceramic element 100 is inserted into an insertion hole 70c of the insulating holder 70.

Also, a first separator 71 formed of an insulating material is disposed on the rear end side GK of the insulating holder 70, and a second separator 72 formed of an insulating material is disposed on the rear end side GK of the first separator 71. Thus, the first and second separators 71 and 72 are arranged in tandem in the longitudinal direction HN, and are accommodated within the inner tube 80.

The first separator 71 has an insertion hole 71c. The ceramic element 100 extends through the insertion hole 71c, and a discharge potential terminal 73 is accommodated in the insertion hole 71c. The second separator 72 has a first insertion hole 72a and a second insertion hole 72b. A rear end portion 100K of the ceramic element 100 (see FIG. 5) is located in the second insertion hole 72b, and an auxiliary potential terminal 75, a first heater terminal 76, and a second heater terminal 77 are accommodated in the second insertion hole 72b.

Notably, within the insertion hole 71c of the first separator 71, the discharge potential terminal 73 is in contact with a discharge potential pad 113 (to be described later) of the ceramic element 100 (see FIGS. 5 and 6). Within the second insertion hole 72b of the second separator 72, the auxiliary potential terminal 75 is in contact with an auxiliary potential pad 125 of the ceramic element 100, the first heater terminal 76 is in contact with a first heater pad 136 of the ceramic element 100, and the second heater terminal 77 is in contact with a second heater pad 137 of the ceramic element 100.

Further, within the first insertion hole 72a of the second separator 72, the discharge potential terminal 73 is connected to an end portion 161t of the discharge potential lead wire 161. Also, within the second insertion hole 72b of the second separator 72, the auxiliary potential terminal 75 is connected to an end portion 162t of the auxiliary potential lead wire 162, the first heater terminal 76 is connected to an end portion 163t of the first heater lead wire 163, and the second heater terminal 77 is connected to an end portion 164t of the second heater lead wire 164.

A sensor GND metal connection member 82 is fitted onto a rear end portion 80k of the inner tube 80, and is laser-welded thereto. The cables 165 to 168 are passed through the sensor GND metal connection member 82. Notably, the inner external conductors 165G1 and 166G1 of the external conductors 165G and 166G of the cables 165 and 166 communicate with the sensor GND metal connection member 82. As a result, all of the inner tube 80, the metallic shell 50, the inner protector 45, and the outer protector 40, which communicate with the sensor GND metal connection member 82, are maintained at the sensor GND potential SGND.

Further, a grommet 84 formed of fluororubber and a chassis GND metal connection member 83 are disposed within a small diameter portion 96 of the outer tube 95 located on the rear end side GK. The cables 165 to 168 are passed through these components. Notably, the outer external conductors 165G2 and 166G2 of the external conductors 165G and 166G of the cables 165 and 166 communicate with the chassis GND metal connection member 83.

The chassis GND metal connection member 83 is crimped together with the small diameter portion 96 of the outer tube 95 so that the diameter of the chassis GND metal connection member 83 decreases. Thus, the grommet 84 and the chassis GND metal connection member 83 are fixed within the small diameter portion 96 of the outer tube 95. As a result, all of the mounting metallic member 90, the outer tube 95, the chassis GND metal connection member 83, which communicate with the exhaust pipe EP and the attachment boss BO, are maintained at the chassis GND potential CGND.

Also, as described above, the chassis GND potential CGND is the same as the GND potential of the battery BT (FIG. 2) mounted on the vehicle AM.

Next, the structure of the ceramic element 100 will be described in detail. As shown in FIGS. 5 and 6, the ceramic element 100 has a plate-shaped insulative ceramic substrate 101 formed of alumina. A discharge electrode member 110, an auxiliary electrode member 120, and a heater portion 130 are embedded in the ceramic substrate 101, and are integrated through firing (integral firing).

More specifically, the ceramic substrate 101 is formed by laminating three ceramic layers 102, 103, and 104 formed of alumina originating from an alumina green sheet, and two insulating cover layers 105 and 106 of alumina are formed between these layers by means of printing. The discharge electrode member 110 is disposed between the insulating cover layer 105 and the ceramic layer 103. Also, the auxiliary electrode member 120 is disposed between the ceramic layer 103 and the insulating cover layer 106, and the heater portion 130 is disposed between the insulating cover layer 106 and the ceramic layer 104. The layers, the members, and the heater portion are integrated together, whereby the ceramic element 100 is formed.

Figure 5:
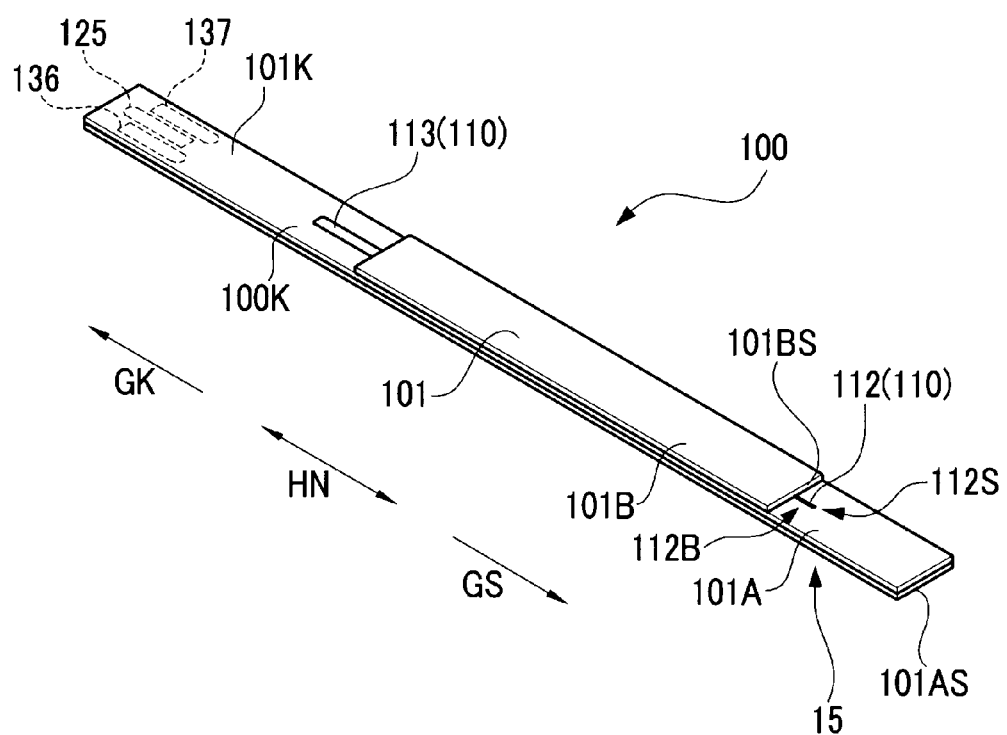
FIG. 5 is a perspective view showing the entirety of a ceramic element of the sensor main body of the particle detection system according to the embodiment.
Figure 6:
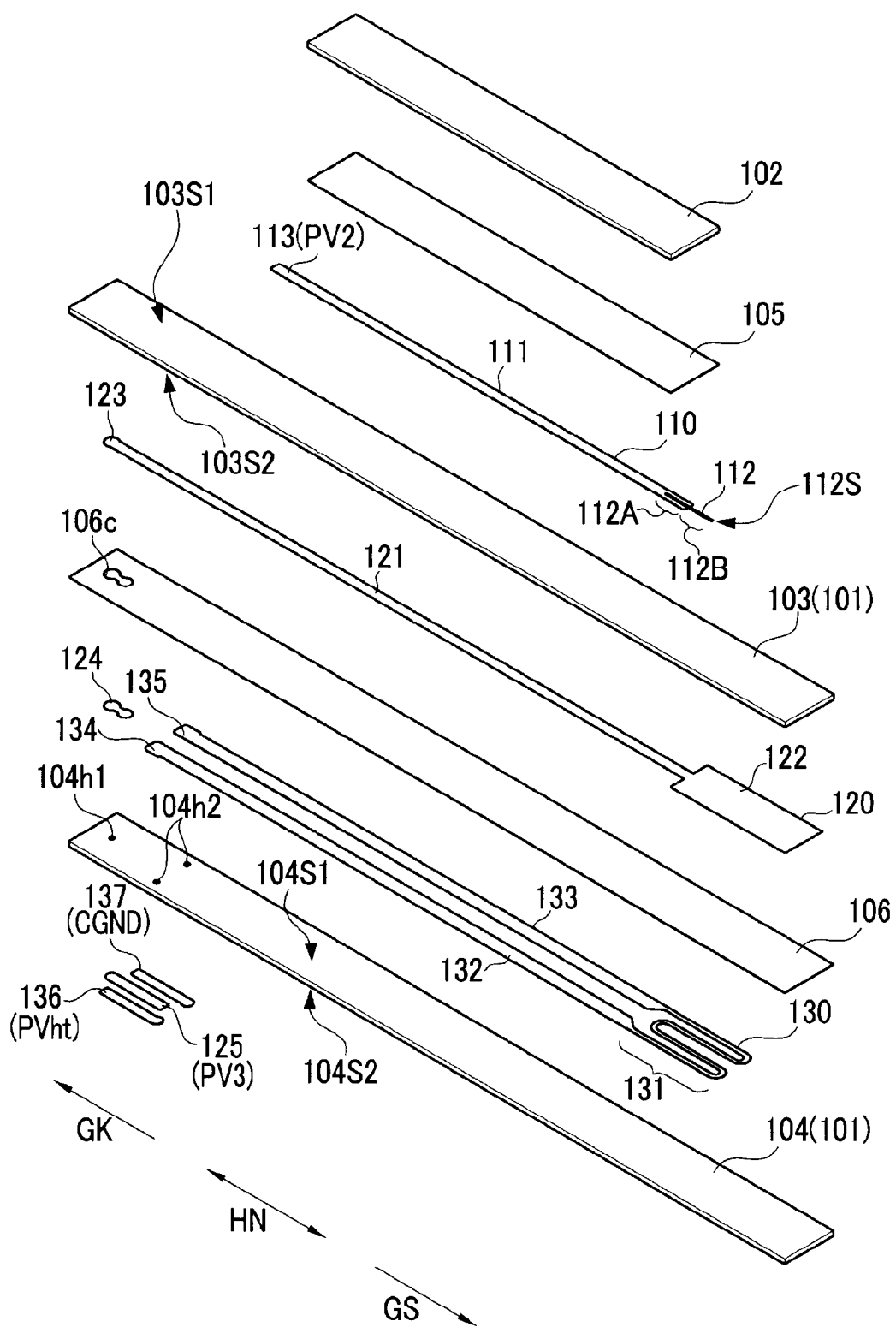
FIG. 6 is an exploded perspective view showing the structure of the ceramic element of the sensor main body of the particle detection system according to the embodiment.

Notably, in the present embodiment, as shown in FIG. 5, the ceramic substrate 101 of the ceramic element 100 has a structure in which a second ceramic portion 101B composed of the ceramic layer 102 and shorter than the ceramic layers 103 and 104 as measured in the longitudinal direction HN is layered on a first ceramic portion 101A composed of the ceramic layers 103 and 104. Also, a second forward end 101BS of the second ceramic portion 101B located on the forward end side GS in the longitudinal direction HN is shifted toward the rear end side GK in the longitudinal direction HN from a first forward end 101AS of the first ceramic portion 101A located on the forward end side GS in the longitudinal direction HN.

In the ceramic element 100, the discharge electrode member 110 extends in the longitudinal direction HN, and has a needle-shaped electrode portion 112 formed of platinum wire, a lead portion 111 electrically communicating with the needle-shaped electrode portion 112 and formed on one surface 103S1 of the ceramic layer 103 by means of pattern printing, and the discharge potential pad 113 electrically communicating with the lead portion 111.

The lead portion 111 of the discharge electrode member 110 and an embedment portion 112A (on the rear end side GK) of the needle-shaped electrode portion 112 connected to the lead portion 111 are covered by the insulating cover layer 105 and the ceramic layer 102 and are embedded in the ceramic substrate 101; specifically, between the ceramic layer 102 and the ceramic layer 103.

Meanwhile, an exposed portion 112B (on the forward end side GS) of the needle-shaped electrode portion 112 formed of platinum wire is exposed from the second forward end 101BS of the second ceramic portion 101B of the ceramic substrate 101. In addition, a needle-shaped distal end portion 112S of the exposed portion 112B located on the forward end side GS and having a tapered shape is bent so that the end of the needle-shaped distal end portion 112S is separated from the surface 103S1 of the ceramic layer 103 by 2 to 3 mm; i.e., the needle-shaped distal end portion 112S projects into the space outside the ceramic substrate 101 while separating from the surface 103S1 of the ceramic layer 103.

The auxiliary electrode member 120 is formed by means of pattern printing and has a rectangular auxiliary electrode portion 122 disposed on the forward end side GS of the ceramic element 100, and an auxiliary electrode lead portion 121 electrically communicating with the auxiliary electrode portion 122 and extending toward the rear end side GK of the ceramic element 100. The auxiliary electrode member 120 (the auxiliary electrode lead portion 121 and the auxiliary electrode portion 122) is formed on a surface 103S2 of the ceramic layer 103 opposite the surface 103S1, and is covered by the insulating cover layer 106.

The auxiliary electrode lead portion 121 of the auxiliary electrode member 120 has an end portion 123 on the rear end side GK. The end portion 123 communicates with a conductor pattern 124 formed on one surface 104S1 of the ceramic layer 104 through a through hole 106c of the insulating cover layer 106. Further, the conductor pattern 124 communicates with an auxiliary potential pad 125 formed on the other surface 104S2 of the ceramic layer 104 through a through hole 104h1 extending through the ceramic layer 104.

Also, the heater portion 130 is formed on the one surface 104S1 of the ceramic layer 104 by means of pattern printing. The heater portion 130 has a heat generation portion 131 which is disposed on the forward end side GS of the ceramic element 100 and generates heat when energized to thereby heat the ceramic element 100, and two heater lead portions 132 and 133 electrically communicating with the heat generation portion 131 and extending toward the rear end side GK of the ceramic element 100. The heater portion 130 is formed on the one surface 104S1 of the ceramic layer 104, and is covered by the insulating cover layer 106.

The heater lead portions 132 and 133 have end portions 134 and 135 on the rear end side GK. The end portions 134 and 135 electrically communicate, through through holes 104h2 extending through the ceramic layer 104, with a first heater pad 136 and a second heater pad 137, respectively, which are formed on the other surface 104S2 of the ceramic layer 104.

Next, detection of particles in the present system 1 will be described.

The discharge electrode member 110, the auxiliary electrode member 120, and the heater 130 of the ceramic element 100 are connected to the circuit section 190 which is not shown in FIG. 3 (see FIGS. 1 and 2) through the discharge potential lead wire 161, the auxiliary potential lead wire 162, the first heater lead wire 163, and the second heater lead wire 164, which are described above. Also, the inner external conductors 165G1 and 166G1 of the cables 165 and 166 are also connected to the first output terminal 211 of the ion source power supply circuit 210 and the auxiliary first output terminal 241 of the auxiliary electrode power supply circuit 240 in the circuit section 190, whereby the inner external conductors 165G1 and 166G1 are maintained at the sensor GND potential SGND. As described above, the inner protector 45 disposed around the portion (ion source 15) of the ceramic element 100 on the forward end side GS is also maintained at the sensor GND potential SGND through the sensor GND metal connection member 82, etc. communicating with the inner external conductors 165G1 and 166G1.

The discharge potential PV2 (see FIGS. 2 and 6), which is a positive high voltage (e.g., 1 to 2 kV), is supplied from the ion source power supply circuit 210 to the needle-shaped electrode portion 112 of the discharge electrode member 110 through the discharge potential lead wire 161, the discharge potential terminal 73, and the discharge potential pad 113. As a result, gaseous discharge; specifically, corona discharge, occurs between the needle-shaped distal end portion 112S of the exposed portion 112B of the needle-shaped electrode portion 112 and the inner protector 45 maintained at the sensor GND potential SGND, whereby ions CP (see FIG. 7) are generated around the needle-shaped distal end portion 112S. As described above, by the action of the outer protector 40 and the inner protector 45, the exhaust gas EG is introduced into the interior of the inner protector 45, and a flow of the introduced exhaust gas EGI from the rear end side GK toward the forward end side GS is produced near the ceramic element 100. Therefore, as shown in FIG. 7, the generated ions CP adhere to particles S contained in the introduced exhaust gas EGI. As a result, the particles S become positively charged particles SC, which flow toward the discharge opening 45O together with the introduced exhaust gas EGI, and are discharged.

Meanwhile, the auxiliary potential PV3 (see FIGS. 2 and 6) set to a predetermined potential (e.g., a positive DC potential of 100 to 200 V) is applied from the auxiliary electrode power supply circuit 240 to the auxiliary electrode portion 122 of the auxiliary electrode member 120 through the auxiliary potential lead wire 162, the auxiliary potential terminal 75 and the auxiliary potential pad 125. Thus, a repulsive force directed from the auxiliary electrode portion 122 toward the inner protector 45 (collection electrode) located on the radially outer side acts on floating ions CPF (see FIG. 7), which are some of the ions CP generated by the ion source 15 and have not adhered to the particles S. As a result, the floating ions CPF are caused to adhere to various portions of the collection electrode (inner protector 45) to thereby assist the collection. Thus, the floating ions CPF can be collected reliably, and the floating ions CPF are prevented from being discharged through the discharge opening 45O.

In the present system 1, a signal (signal current Is) corresponding to the amount of charge of discharged ions CPH adhering to the electrified particles SC discharged through the discharge opening 45O is detected by the signal current detection circuit 230. As a result, the amount (concentration) of the particles S contained in the exhaust gas EG can be detected properly.

Notably, as described above, in the present embodiment, the inner protector 45 around the ceramic element 100 (ion source 15) is maintained at the sensor GND potential SGND, and corona discharge is generated between the ceramic element 100 and the inner protector 45. Additionally, the inner protector 45 serves as a collection electrode as well. Namely, in the present embodiment, the collection potential for performing collection by the inner protector 45 (collection electrode) is equal to the sensor GND potential SGND.

In the present embodiment, as shown by a broken line in FIG. 7, the portion of the ceramic element 100 on the forward end side GS, which forms the ion source 15, a portion (side trunk portion 46) of the inner protector 45 located around the ion source 15, and a space VO between the ion source 15 and the side trunk portion 46 of the inner protector 45 constitute an electrification section 11 which electrifies the particles S contained in the exhaust gas EG to thereby produce the electrified particles SC (see FIG. 7). Accordingly, in the present embodiment, the electrification section 11 contains the ion source 15.

Figure 8:
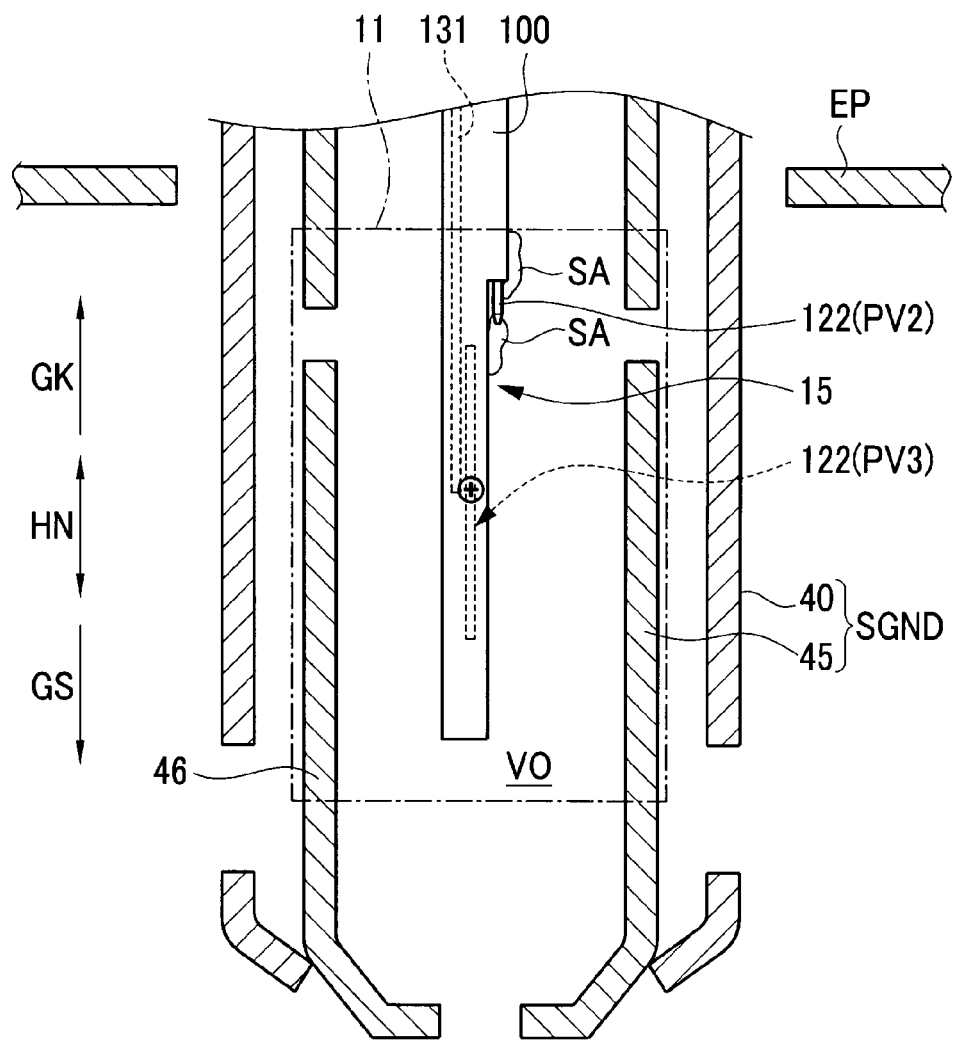
FIG. 8 is an explanatory view showing particles adhering to an ion source of the particle detection system according to the embodiment and a heating section for heating the particles.

Also, the heater energization circuit 226 of the measurement control circuit 220 applies a predetermined heater energization voltage between the first heater pad 136 and the second heater pad 137 through the first heater lead wire 163 and the first heater terminal 76, and the second heater lead wire 164 and the second heater terminal 77. As a result, the heat generation portion 131 of the heater portion 130 generates heat upon energization so as to heat the ion source 15 of the ceramic element 100 to thereby remove adhering particles SA; i.e., soot (particles S) adhering to the ceramic element 100 (ion source 15) (see FIG. 8). Thus, the insulation properties of the ion source 15 having deteriorated can be recovered.

Specifically, a pulse voltage obtained from the battery voltage (DC 12 V or 24 V) of the battery BT of the vehicle AM through PWM control performed by the heater energization circuit 226 is applied as the heater energization voltage. For example, a first heater potential PVht which is applied to the first heater pad 136 through the first heater lead wire 163 and the first heater terminal 76 is a positive side potential of the pulse voltage obtained from the battery voltage (DC 12 V or 24 V) through PWM control. Also, a second heater potential which is applied to the second heater pad 137 through the second heater lead wire 164 and the second heater terminal 77 is the chassis GND potential CGND which is the same as the GND potential of the battery BT (see FIGS. 2 and 6).

Incidentally, the particles S (soot) contained in the exhaust gas EG are likely to accumulate and adhere to (are likely to become adhering particles SA at) a portion of the ceramic element 100, serving as the ion source 15, at which corona discharge occurs; i.e., the discharge electrode member 110 (particularly, the vicinity of the exposed portion 112B of the needle-shaped electrode portion 112) or the like. In order to remove the adhering particles SA, the ion source 15 of the ceramic element 100 is heated by the heater portion 130 to a temperature at which the adhering particles SA burn. As a result, the adhering particles SA (soot) adhering to the ion source 15 are burned and removed (see FIG. 8).

However, the system 1 of the present embodiment is used for the vehicle AM on which a direct-injection-type gasoline engine is mounted as the engine ENG. As described above, in the case of a gasoline engine, combustion is basically performed at the stoichiometric air-fuel ratio. Therefore, in the case where the air-fuel ratio is on the rich side of the stoichiometric air-fuel ratio, oxygen is hardly present in the exhaust gas EG. In such exhaust gas EG in which oxygen is hardly present, even when the heater portion 130 is energized to generate heat, the soot adhering to the ion source 15 cannot be burned.

In addition, in the case where electricity is always supplied to the heater portion 130 so as to allow the heater portion 130 to burn adhering particles at any time, useless energy consumption (power consumption) occurs at the heater portion 130.

Figure 2:
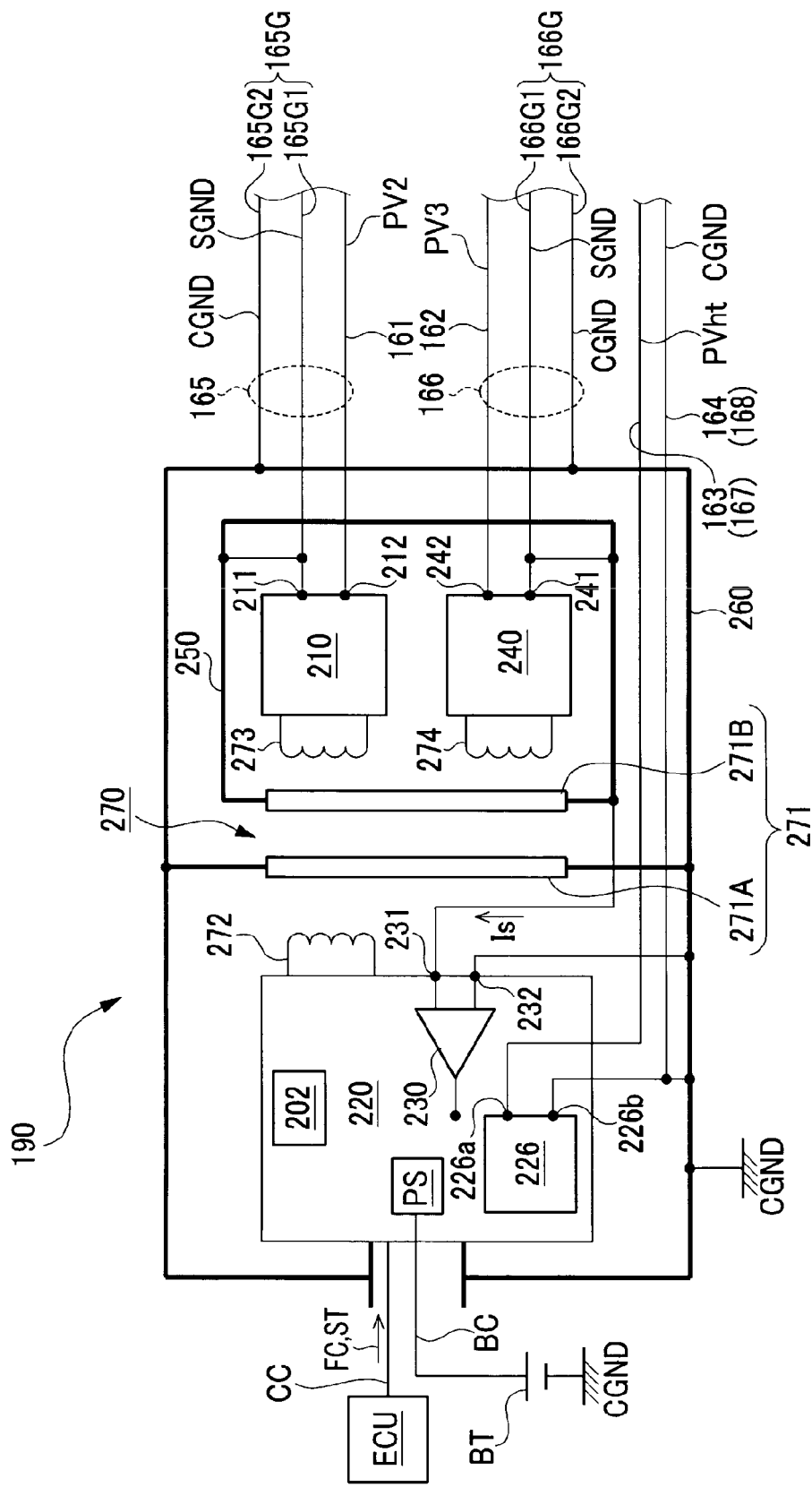
FIG. 2 is an explanatory view schematically showing the configuration of a circuit section of the particle detection system according to the embodiment.

In order to overcome such a problem, in the system 1 of the present embodiment, the microprocessor 202 of the measurement control circuit 220 detects input of a fuel cut signal FC which is transmitted from the engine control unit ECU of the vehicle AM through the CAN bus (see FIG. 1) and shows that the engine ENG of the vehicle AM is in a fuel cut period (see FIG. 2). The microprocessor 202 supplies electricity to the heater portion 130 in accordance with this fuel cut signal FC by using the heater energization circuit 226.

During the fuel cut period, as a result of stoppage of the supply of fuel to the engine ENG, instead of combustion gas, air (outside air) flows through the exhaust pipe EP. Accordingly, the exhaust gas EG contains oxygen at a concentration at which soot burns. Therefore, the adhering particles SA (soot) adhering to the ion source 15 can be properly burned and removed by supplying electricity to the heater portion 130 during this fuel cut period to thereby heat the ion source 15 to a temperature at which soot burns.

Figure 9:
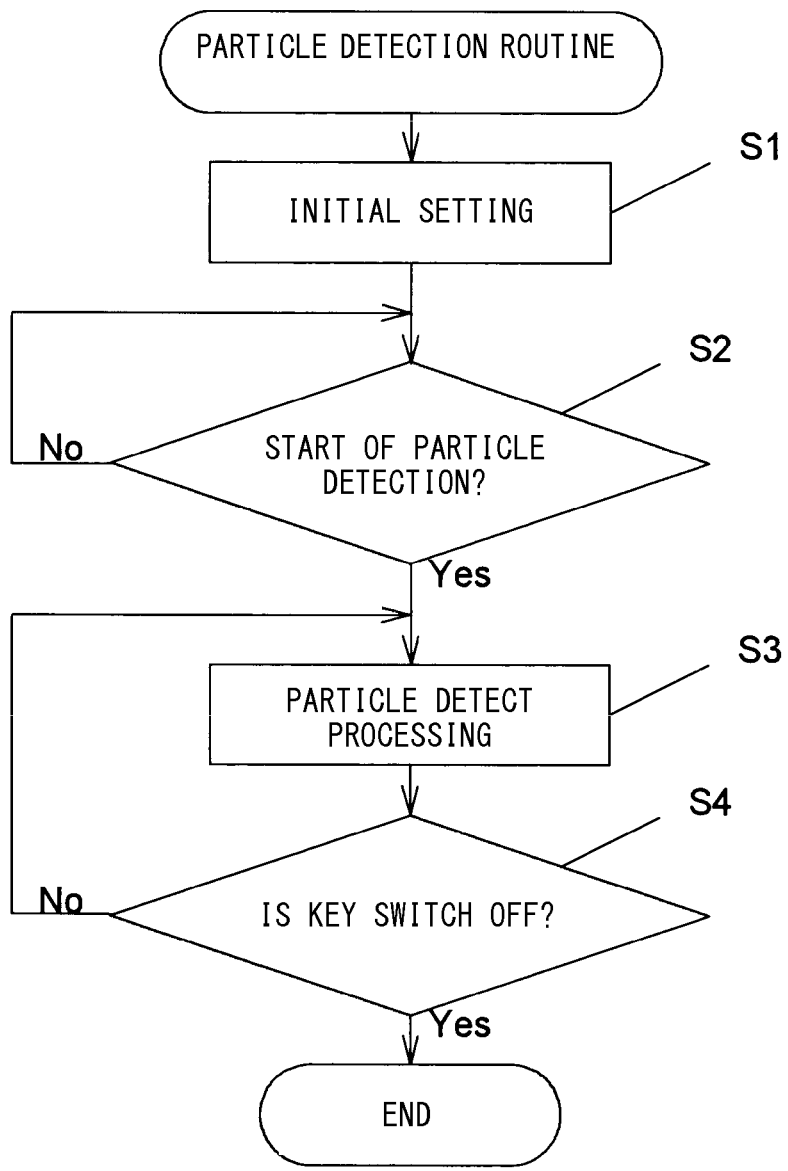
FIG. 9 is a flowchart showing operation of a microprocessor of the particle detection system according to the embodiment at the time when the microprocessor executes a particle detection routine for performing particle detection processing.
Figure 10:
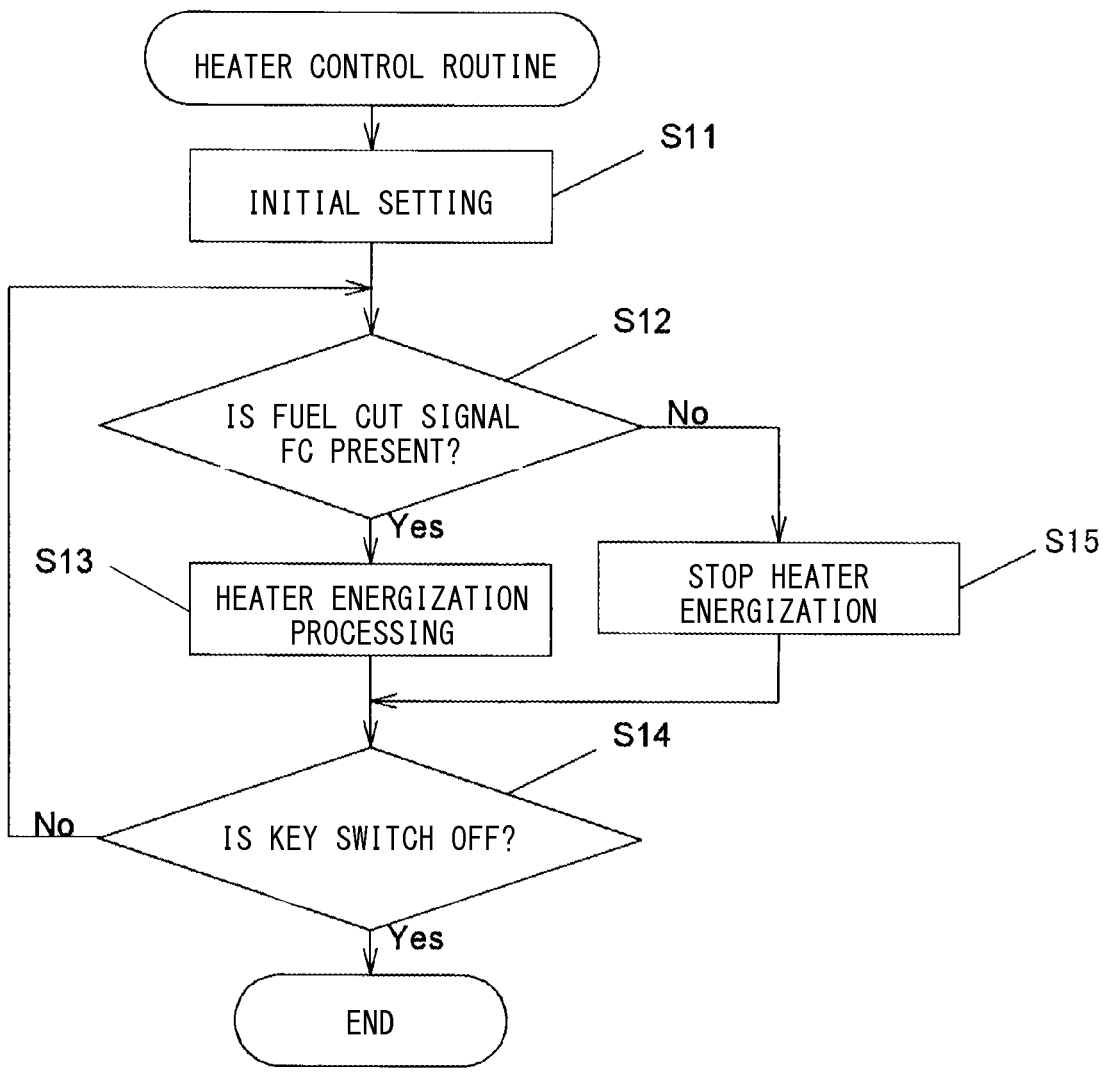
FIG. 10 is a flowchart showing operation of the microprocessor of the particle detection system according to the embodiment at the time when the microprocessor executes a heater control routine for performing heater energization processing.

Next, of the operation of the system 1 of the present embodiment, the operation of the microprocessor 202 which executes particle detection processing and heater energization processing will be described with reference to the flowchart of a particle detection routine shown in FIG. 9 and the flowchart of a heater control routine shown in FIG. 10. Notably, the microprocessor 202 executes the particle detection routine and the heater control routine in parallel.

First, the particle detection routine shown in FIG. 9 will be described.

When the key switch (not shown) of the engine ENG is turned on, the present system 1 (the microprocessor 202 of the measurement control circuit 220) is started. First, in step S1, the microprocessor 202 performs initial setting necessary for particle detection. After that, in step S2, the microprocessor 202 determines whether or not an instruction signal ST (see FIG. 2) which instructs the start of particle detection is output from the ECU.

In the case where the particle detection start instruction signal ST is not output from the ECU (No), the microprocessor 202 repeats step S2 so as to wait for the input of the particle detection start instruction signal ST from the ECU. When the microprocessor 202 detects the particle detection start instruction signal ST from the ECU (Yes), the microprocessor 202 proceeds to step S3.

In step S3, the microprocessor 202 performs predetermined particle detection processing; i.e., processing of applying the high voltage generated by the ion source power supply circuit 210 to the ion source 15 to thereby produce ions CP by means of corona discharge, and detecting the signal current Is corresponding to the amount of charge of the discharged ions CPH by using the signal current detection circuit 230.

In step S4 subsequent thereto, the microprocessor 202 determines whether or not the key switch of the engine ENG is turned off. In the case where the key switch of the engine ENG is not turned off (No), the microprocessor 202 returns to step S3 and continues the particle detection processing. Meanwhile, the case where the key switch of the engine ENG is turned off (Yes), the microprocessor 202 ends the particle detection processing.

Next, the heater control routine shown in FIG. 10 will be described.

When the microprocessor 202 is started, in step S11, the microprocessor 202 first performs initial setting necessary for heater energization.

Next, in step S12, the microprocessor 202 determines whether or not the fuel cut signal FC output from the ECU is input through the CAN bus. Thus, the microprocessor 202 determines whether or not the engine ENG of the vehicle AM is in a fuel cut period. In the case where the fuel cut signal FC is not input (No); i.e., when the engine ENG is not in a fuel cut period, the microprocessor 202 proceeds to step S15 so as to stop the heater energization processing, and then proceeds to step S14. Notably, in the case where the heater energization processing is performed in step S13, in step S15, the microprocessor 202 stops that processing. However, in the case where the heater energization processing is not performed in step S13, the microprocessor 202 maintains the state in which the heater energization processing is not performed and proceeds to step S14.

Meanwhile, in the case where the fuel cut signal FC is input (Yes); i.e., when the engine ENG is in a fuel cut period, the microprocessor 202 proceeds to step S13 and supplies electricity to the heater portion 130 by using the heater energization circuit 226. Specifically, the microprocessor 202 applies the pulse voltage obtained through PWM control to the heater portion 130, to thereby heat the ceramic element 100 to a predetermined temperature at which soot adhering to the ion source 15 (the ceramic element 100) can burn.

After that, the microprocessor 202 proceeds to step S14 and determines whether or not the key switch of the engine ENG is turned off. In the case where the key switch of the engine ENG is not turned off (No), the microprocessor 202 returns to step S12, and again detects the input of the fuel cut signal FC and continues the heater energization processing. Meanwhile, in the case where the key switch of the engine ENG is turned off (Yes), the microprocessor 202 ends the heater energization processing.

In the present embodiment, the fuel cut period of the engine ENG of the vehicle AM is the burnable period, and the fuel cut signal FC from the ECU corresponds to the burnable signal. The microprocessor 202 of the measurement control circuit 220 which detects the input of the fuel cut signal FC from the ECU (namely, the microprocessor 202 executing step S12) corresponds to the period detection means. Also, the microprocessor 202 of the measurement control circuit 220 which energizes the heater portion 130 according to the fuel cut signal FC (namely, the microprocessor 202 executing step S13) and the heater energization circuit 226 of the measurement control circuit 220 correspond to the heater energization control means.

Also, of the heater energization control means, the microprocessor 202 executing step S13 and the heater energization circuit 226 correspond to the energization switching means for switching the supply of electricity to the heater portion 130.

As described above, in the system 1 of the present embodiment, the fuel cut period is detected, and energization of the heater portion 130 is performed during this fuel cut period so as to heat the ion source 15 of the electrification section 11 to a temperature at which soot (adhering particles SA) adhering thereto burns (step S13). As a result, the soot (adhering particles SA) adhering to the ion source 15 can be removed properly, whereby the detection performance of the sensor main body 10 can be maintained. Meanwhile, since the heater portion 130 is not energized at all times, unnecessary energy consumption (power consumption) at the heater portion 130 can be suppressed.

Also, in the present embodiment in which the present system 1 is applied to a vehicle on which a gasoline engine is mounted, soot (adhering particles SA) can be removed properly and the detection performance of the sensor main body 10 can be maintained.

Further, in the system 1 of the present embodiment, the input of the fuel cut signal FC from the ECU is detected, and the energization of the heater portion 130 is switched in accordance with the detected fuel cut signal FC. Therefore, it is possible to reliably burn and remove the soot (adhering particles SA) adhering to the ion source 15 by energizing the heater portion 130 at a proper timing.

Also, since the burnable period can be known from the fuel cut signal FC output from the ECU and representing the fuel cut period, it is possible to properly burn and remove the soot (adhering particles SA) adhering to the ion source (the electrification section).

The present invention has been described on the basis of the embodiment. However, the present invention is not limited to the above-described embodiment and may be appropriately modified for application without departing from the gist of the invention.

For example, in the embodiment, the present invention is applied to a particle detection system in which the electrification section for electrifying the particles S to thereby produce the electrified particles SC is the ion source 15 which generates the ions CP by means of gaseous discharge. However, the electrification section of the sensor main body is not limited thereto. For example, the present invention may be applied to a particle detection system whose sensor main body has an electrification section in which particles are caused to adhere to the surface of an electrode and a high voltage is applied to the electrode so as to electrify the particles S to thereby produce electrified particles SC (see Patent Documents 2 and 3). In this case, an example of the heater portion is a heater portion which heats the electrode of the electrification section to which the particles adhere.

Also, in the embodiment, the fuel cut period of the engine ENG of the vehicle AM is detected as the burnable period. However, an idling stop period of the engine ENG of the vehicle AM (period during which the engine ENG is automatically stopped when the vehicle temporarily stops, for example, until a traffic light changes) or a lean burn operation period (period during which the engine ENG is operated by lean burn at an air-fuel ratio on the lean side with respect to the stoichiometric air-fuel ratio) may be detected as the burnable period. Namely, the microprocessor 202 of the circuit section 190 may detect through the CAN bus a signal which is output from the ECU and showing that the engine ENG of the vehicle AM in an idling stop period or a lean burn operation period.

Also, in the case of a hybrid vehicle, the microprocessor 202 may detect a signal representing a period during which the engine stops and the vehicle is traveling by a motor. During a period during which the vehicle is traveling by the motor, the engine is stopped, and instead of combustion gas, air (outside air) flows through the exhaust pipe EP. Therefore, the period during which the vehicle is traveling by the motor also corresponds to the burnable period.

Also, in the embodiment, the fuel cut signal FC output from the ECU onto the CAN bus is detected as the burnable signal. However, the embodiment may be modified to detect a burnable period during which the oxygen concentration of the exhaust gas EG is equal to or higher than a predetermined level by utilizing the output of an oxygen sensor which is attached to the exhaust pipe EP and measures the oxygen concentration of the exhaust gas EG.

Figure 11:
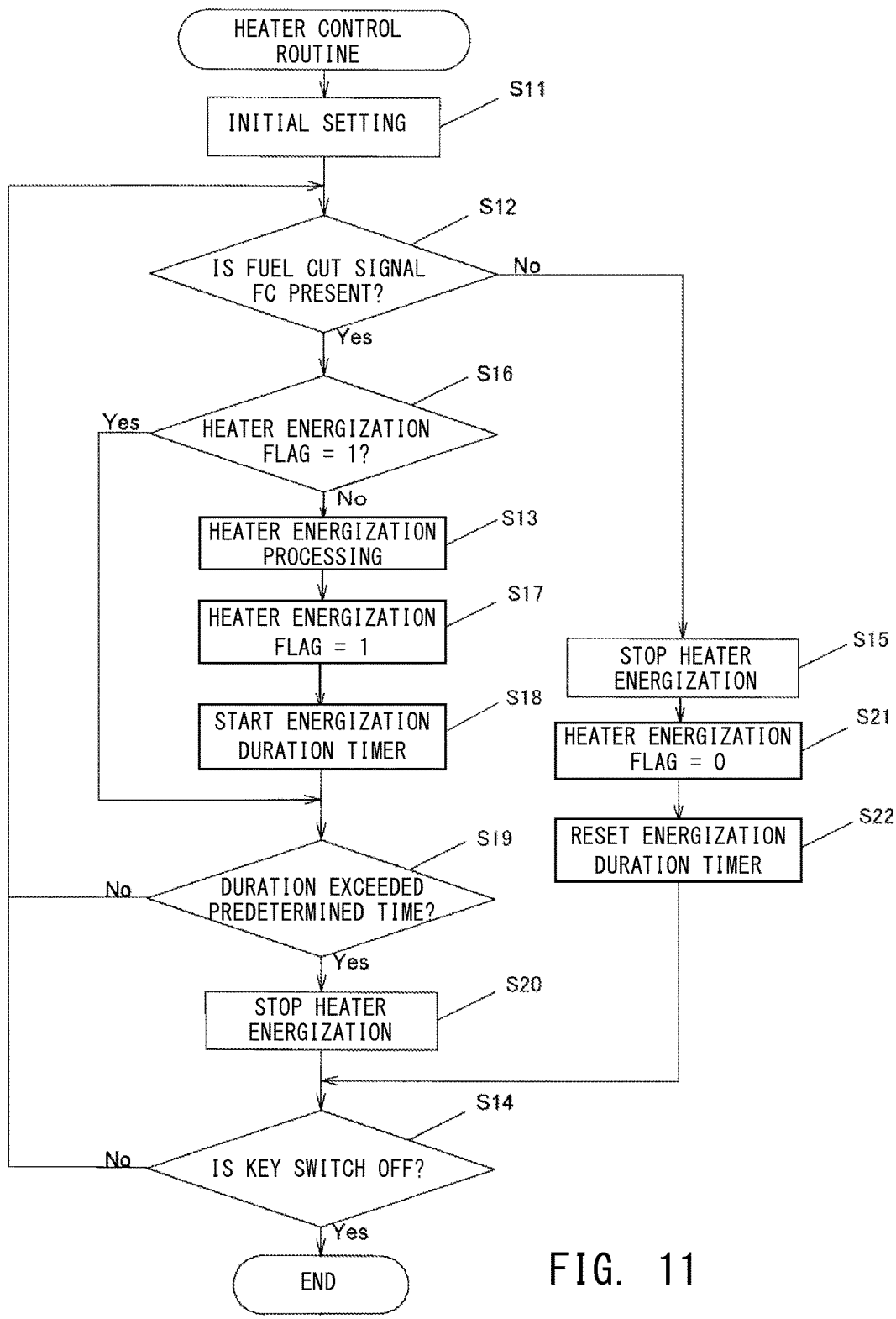
FIG. 11 is a flowchart showing operation of the microprocessor according to a modification at the time when the microprocessor executes the heater control routine for performing heater energization processing.

Also, the heater control routine executed by the microprocessor 202 is not limited to the processing of the above-described embodiment which has been described with reference to FIG. 10. A modification of the heater control routine executed by the microprocessor 202 will be described with reference to FIG. 11.

When the microprocessor 202 is started, the microprocessor 202 performs steps S11 and S12 which are the same as those of the above-described embodiment. In this modification, in the case where the microprocessor 202 determines in step S12 that the fuel cut signal FC is input (Yes), i.e., the engine is in the fuel cut period, the microprocessor 202 proceeds to step S16 and determines whether or not a heater energization flag is "1." In the case where the microprocessor 202 does not determine in step S16 that the heater energization flag is "1" (No); i.e., in the case where the heater energization flag is "0," the microprocessor 202 proceeds to step S13 so as to execute (start) processing of energizing the heater portion 130. Notably, the processing of this step S13 is the same as the processing of step S13 of the above-described embodiment.

Next, the microprocessor 202 proceeds to step S17 and sets the heater energization flag to "1." Subsequently, the microprocessor 202 proceeds to step S18 so as to start a timer for clocking the duration time of energization of the heater portion 130 and then proceeds to step S19. Meanwhile, in the case where the microprocessor 202 determines in step S16 that the heater energization flag is "1" (Yes), the microprocessor 202 proceeds to step S19 by skipping steps S13, S17, and S18.

In step S19, the microprocessor 202 determines whether or not the duration time of energization of the heater portion 130 (duration timer) has exceeded a predetermined time. Notably, a time within which soot adhering to the ion source 15 (the electrification section 11) can be burnt through heating by the heater portion 130 is set as the predetermined time. In the case where the microprocessor 202 determines in step S19 that the energization duration time has exceeded the predetermined time (Yes), the microprocessor 202 proceeds to step S20 and stops the energization of the heater portion 130 by the heater energization circuit 226. At that time, the microprocessor 202 neither sets the heater energization flag to "0" nor resets the timer. Therefore, even when the detection of the input of the fuel cut signal FC continues after the energization of the heater portion 130 has been stopped in step S20, the affirmative determination (Yes) in step S12, the affirmative determination (Yes) in step S16, and the negative determination (No) in step S19 are repeated, so that the processing of energizing the heater portion 130 is not executed. Meanwhile, in the case where the microprocessor 202 determines in step S19 that the energization duration time has not exceeded the predetermined time (No), the microprocessor 202 returns to step S12. After completion of the processing of step S20, the microprocessor 202 proceeds to step S14. Since the processing of step S14 is the same as the processing of step S14 of the above-described embodiment, its description is omitted.

In the case where the microprocessor 202 determines in step S12 that the fuel cut signal FC is not input (No); i.e., the engine is not in the fuel cut period, the microprocessor 202 proceeds to step S15. Notably, the processing of step S15 is the same as the processing of step S15 of the above-described embodiment. Subsequently, the microprocessor 202 proceeds to step S21 and sets the heater energization flag to "0." As a result, in the case where the microprocessor 202 again detects the input of the fuel cut signal FC, the microprocessor 202 makes the negative determination (No) in step S16, whereby it becomes possible to execute the processing of energizing the heater portion 130 in step S13. Subsequently, the microprocessor 202 proceeds to step S22 so as to reset the timer for clocking the duration time of energization of the heater portion 130 and then proceeds to step S14.

As a result of the heater control routine according to the modification being executed as described above, the heater portion 130 is energized during the fuel cut period so as to heat the ion source 15 of the electrification section 11. Thus, the temperature of the ion source 15 is increased to a temperature at which the soot (adhering particles SA) adhering thereto burns, whereby the soot (adhering particles SA) adhering to the ion source 15 can be removed properly. When the duration time of energization of the heater portion 130 exceeds the predetermined time, the energization of the heater portion 130 is stopped even if it is in the middle of the fuel cut period (step S20). Therefore, the present modification has a merit that the useless energy consumption (power consumption) at the heater portion can be further suppressed as compared with the above-described embodiment. Notably, the microprocessor 202 executing step S20 corresponds to the energization stoppage means for stopping the energization of the heater portion 130.

DESCRIPTION OF REFERENCE CHARACTERS

AM: vehicle
ENG: engine (internal combustion engine)
EP: exhaust pipe
EG: exhaust gas (gas under measurement)
CGND: chassis GND potential (second heater potential)
SGND: sensor GND potential
PV2: discharge potential
PV3: auxiliary potential
PVht: first heater potential
S: particle
SC: electrified particle
SA: adhering particle
CP: ion
CPF: floating ion
GS: forward end side
GK: rear end side
HN: longitudinal direction
1: particle detection system
10: sensor main body
11: electrification section
15: ion source
40: outer protector
45: inner protector
50: metallic shell
71: first separator
72: second separator
73: discharge potential terminal
75: auxiliary potential terminal
76: first heater terminal
77: second heater terminal
80: inner tube
90: mounting metallic member
95: outer tube
100: ceramic element
100K: rear end portion (of ceramic element)
101: ceramic substrate
110: discharge electrode member
120: auxiliary electrode member
130: heater portion
190: circuit section
210: ion source power supply circuit
220: measurement control circuit
226: heater energization circuit (heater energization control means, energization switching means)
230: signal current detection circuit
240: auxiliary electrode power supply circuit
FC: fuel cut signal
S13, S15: period detection means, signal detection means
S14 to S16: heater energization control means
S14, S16: energization switching means

The invention claimed is:

1. A particle detection system which includes a sensor main body having an electrification section configured for electrifying particles contained in a gas under measurement so as to produce electrified particles and which detects the particles contained in the gas under measurement by using the electrified particles, wherein
the sensor main body has a heater portion configured for heating at least a portion of the electrification section; and
the particle detection system comprises:
period detection means configured for detecting a burnable period during which the gas under measurement contains oxygen for burning particles adhering to the electrification section, and
heater energization control means configured for energizing the heater portion during the burnable period so as to heat at least a portion of the electrification section to a temperature at which the particles adhering to the electrification section burn.

2. A particle detection system according to claim 1, wherein
the electrification section includes an ion source configured for producing ions through gaseous discharge and causes the produced ions to adhere to the particles floating in the gas under measurement to thereby electrify the particles and produce the electrified particles; and
the heater portion heats at least a portion of the ion source of the electrification section.

3. A particle detection system according to claim 1, wherein
the period detection means is signal detection means configured for detecting input of a burnable signal externally supplied and indicating the burnable period; and
the heater energization control means includes energization switching means configured for switching the state of supply of electricity to the heater portion in accordance with the detected burnable signal.

4. A particle detection system according to claim 3, wherein
the gas under measurement is exhaust gas discharged from an internal combustion engine; and
the burnable signal is a signal indicating that the internal combustion engine is in a fuel cut period, an idling stop period, or a lean burn operation period.

5. A particle detection system according claim 1, wherein the heater energization control means includes energization stoppage means configured for stopping the energization when a duration time of the energization of the heater portion having started in the burnable period exceeds a predetermined time.

* * * * *